(12) United States Patent
Li et al.

(10) Patent No.: US 11,435,287 B2
(45) Date of Patent: Sep. 6, 2022

(54) SPECTROSCOPIC MEASUREMENTS AND SUPER-RESOLUTION IMAGING BY SUPRACENCE

(71) Applicant: Washington State University, Pullman, WA (US)

(72) Inventors: Alexander Dequan Li, Pullman, WA (US); Wei Wan, Pullman, WA (US)

(73) Assignee: WASHINGTON STATE UNIVERSITY, Pullman, WA (US)

(*) Notice: Subject to any disclaimer, the term of this patent is extended or adjusted under 35 U.S.C. 154(b) by 501 days.

(21) Appl. No.: 16/655,428

(22) Filed: Oct. 17, 2019

(65) Prior Publication Data
US 2020/0124533 A1 Apr. 23, 2020

Related U.S. Application Data

(60) Provisional application No. 62/748,096, filed on Oct. 19, 2018.

(51) Int. Cl.
*G01N 21/64* (2006.01)
*G01N 33/483* (2006.01)
*G01N 15/14* (2006.01)

(52) U.S. Cl.
CPC ..... *G01N 21/6428* (2013.01); *G01N 15/1434* (2013.01); *G01N 21/6458* (2013.01); *G01N 33/4833* (2013.01); *G01N 2021/6417* (2013.01); *G01N 2021/6439* (2013.01); *G01N 2021/6471* (2013.01); *G01N 2201/06113* (2013.01); *G01N 2201/08* (2013.01)

(58) Field of Classification Search
None
See application file for complete search history.

(56) References Cited

PUBLICATIONS

Wan et al. ("Molecular Supracence Resolving Eight Colors in 300-nm Width:Unprecedented Spectral Resolution,"Angew. Chem. Int. Ed.2020,59, 21915-21919). (Year: 2020).*

* cited by examiner

*Primary Examiner* — David P Porta
*Assistant Examiner* — Meenakshi S Sahu
(74) *Attorney, Agent, or Firm* — WC&F IP

(57) ABSTRACT

Application of a new light-molecule interaction in which molecules enable emission of photons with more energy than that of the absorbed photons achieves higher resolution than fluorescence imaging. This emission phenomenon is termed supracence and is applied to obtain more information about the structure and properties of a specimen than currently possible with fluorescence imaging techniques. Because supracence originates from chemical bonds, any structure that contains chemical bonds meets the necessary condition to potentially emit supracence. Super spectral resolution images are achieved by selectively exciting a target molecule to suprace without exciting another fluorophore that has absorption and emission rather close to the target.

39 Claims, 12 Drawing Sheets

SPECTROSCOPIC MEASUREMENTS AND SUPER-RESOLUTION IMAGING BY SUPRACENCE

CROSS-REFERENCE TO RELATED APPLICATIONS

This application claims the benefit of U.S. Provisional Patent Application No. 62/748,096, filed Oct. 19, 2018, the complete contents of which are herein incorporated by reference.

STATEMENT REGARDING FEDERALLY SPONSORED RESEARCH AND DEVELOPMENT

This invention was made with government support under grant no. 1744362 awarded by National Science Foundation. The government has certain rights in the invention.

BACKGROUND OF THE INVENTION

Field of the Invention

The present invention generally relates to super-resolution imaging and, more particularly, to the application of a new light-molecule interaction in which molecules enable emission of photons with more energy than that of the absorbed photons. This emission phenomenon is termed "supracence" and is applied to obtain more information about the structure of a specimen than currently possible with fluorescence imaging techniques. Because supracence originates from chemical bonds, any structure contains chemical bonds meet the necessary condition to potentially emit supracence.

Background Description

Optical wavelength multiplexing is a revolutionary technology enabling exceptionally large volume of information transmitted in a single optical fiber. This concept is naturally adopted in fluorescence imaging, which is considered as the method of choice in the studies of living mechanisms in biological cells because of its ultra sensitivity and minimal invasiveness. Fluorescence imaging has become the method of choice when exploring living mechanisms and functions of biological cells. Among myriad studies, it has shed light on nanostructural information from protein periodic nanostructures, assembly or disassembly actin polymers, interplays of various proteins, and organelle transportations. Fluorescent properties are so versatile that various innovative approaches enable an array of methodologies for producing super-resolution images, such stimulated emission depletion (STED), photoactivated localization microscopy (PALM), and stochastic optical reconstruction microscopy (STORM). The development of STED microscopy earned Stefan W. Hell the Nobel Prize in Chemistry in 2014, awarded for the development of super-resolution techniques. These technologies along with other similar approaches have generated a wave of tremendous interests in super resolution.

Fluorescence emission, however, possesses broad and featureless bands, making very inefficient wavelength multiplexing. This is an unsolvable problem when considering the guidance of current fluorescence principles. Fluorescence technologies result in hot fluorophores because they absorb high-energy photons and emit low-energy photons ($v_{ABS} > v_{EM}$); the energy difference is absorbed by the fluorophores as heat. The hot emitters certainly will impart thermal properties or limitations on the phenomena of photonic emission, which are currently unknown. Within the linear optical field, moreover, it is not regarded possible to emit a photon that has more energy than the value of the absorbed photon, i.e., $v_{ABS} < v_{EM}$.

SUMMARY OF THE INVENTION

Understanding that a molecule is a dynamic cluster held together by the invisible forces known as "bonds", quantum energy of molecular bonds and molecular potential energy created by the variation of the forces can exchange constantly. The emission from exciting a bond can siphon energy from dynamic potentials and thus the emitted photons can have higher energy than that of the absorbed photons; such emission is defined as "supracence". Unlike fluorescence, both supracence excitation and supracence emission are highly specific to a narrow region of the optical spectrum. Therefore, one can selectively excite a target molecule to suprace without exciting another fluorophore that has absorption and emission rather close to the target. Using these new and superior properties of supracence, we can address long felt needs in the market and scientific community.

It is therefore an object of the present invention to provide super spectral resolution images and other instrumental methods by selectively exciting a target molecule to suprace without exciting another fluorophore that has absorption and emission rather close to the target.

According to the invention, we apply of a new light-molecule interaction in which molecules enable emission of photons with more energy than that of the absorbed photons achieves superior spectral resolution than fluorescence. This emission phenomenon, termed supracence, is applied to obtain more information about the structure of a specimen than currently possible with fluorescence imaging techniques. In addition to superior spectral resolution, super spatial resolution images are also achieved by selectively exciting a target molecule to suprace without exciting other fluorophores that has absorption and emission rather close to the target.

This invention concerns molecular absorption and emission, and should not be confused with Raman effect, which is based on inelastic scattering of photons. In Raman processes, light does not excite the molecule, rather it polarizes the electron cloud to produce the inelastic scattering. In molecular absorption and emission, however, photons are absorbed, thus disappeared, and the photon's energy excites the molecules into excited states that have measurable lifetimes before the excited state emits a new photon. In supracence, the new photon has more energy than that of the absorbed photon. Supracence can be further distinguished from other absorption-emission processes because it starts from the lowest electronic state and the lowest vibrational state and arrives at the excited state in a single step as verified by the linearity between excitation power and supracence intensity.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION THE INVENTION

Understanding that a molecule is a dynamic cluster held together by the invisible forces known as "bonds", the inventors recently developed the energy-exchange theory, which states that quantum energy of molecular bonds and molecular potential energy created by the variation of the bonding forces can exchange constantly. This theory predicts that emission can siphon energy from dynamic potentials and thus the emitted photons can have more energy than that of absorbed photons; such emission is defined as supracence emission hereafter for discussions. Unlike fluorescence, both supracence excitation and supracence emission are highly specific to a narrow region of their optical spectra. Therefore, one can selectively excite a target molecule to suprace without exciting another fluorophore that has absorption and emission rather close to the target. Using these properties of supracence, we have demonstrated that two dyes, Rhodamine B derivative and Rhodamine 123, which have absorption and emission maximums only 32 nm apart, were effectively separated and specifically imaged with no measurable crosstalk—an unprecedented paradigm of spectral resolution.

Figure 1:
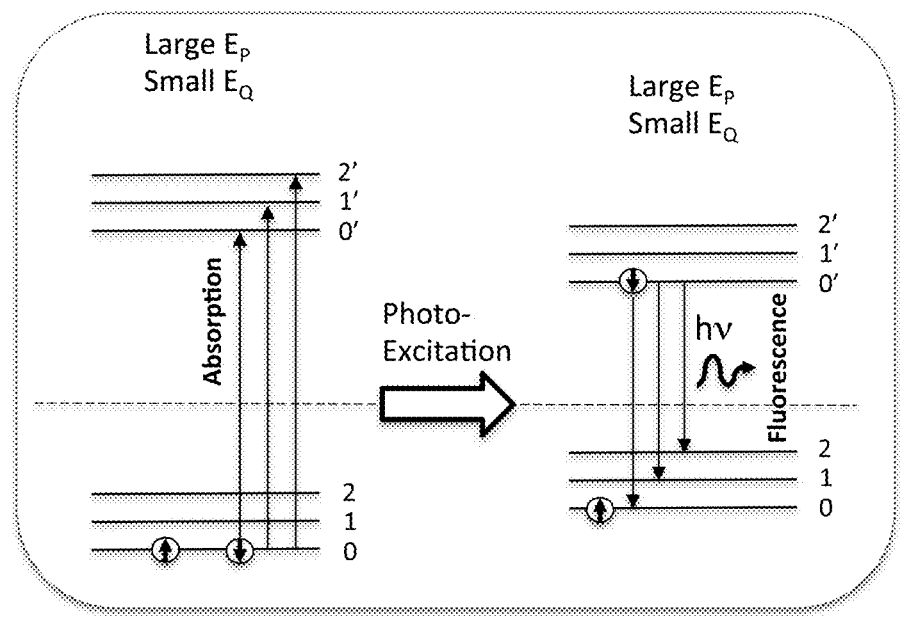
FIG. 1 is a Joblonski diagram that illustrates the electronic states of a molecule and the transitions between if fluorescence.
Figure 2:
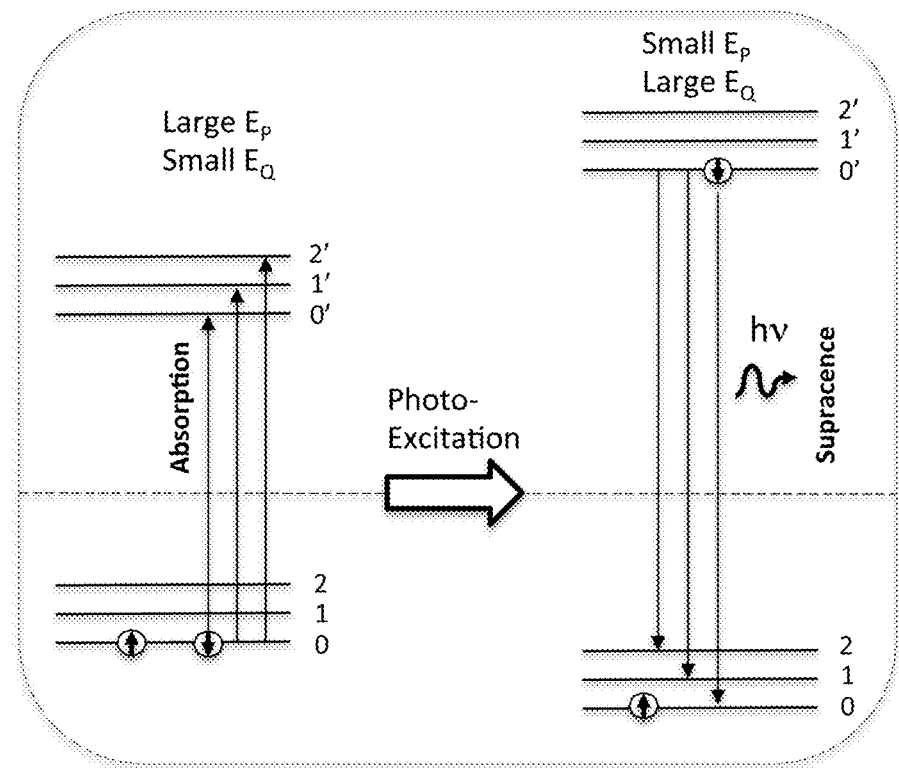
FIG. 2 is a modified Joblonski diagram showing supracence.

Light-molecule interaction is ultimately important because studying these phenomena has yielded rich information about molecular structures, electronic structures, and fluorescence imaging. In most theoretical and experimental models, the molecules have been treated as static particles or with limited dynamics. For example, they can only relax toward structures with smaller emission gaps for radiative decays in fluorescence. Experimental results are a reminder to keep an open mind about possibly unimaginable light-molecule interacting processes beyond intuition. After considerable efforts, the inventors arrived at the conclusions that under specific conditions molecular dynamics in energetic directions opposite of fluorescence must exist. Thus, this disclosure updates Jablonski diagram, see FIG. 1, to Li diagram that describes a significantly more complete picture of molecular excitation and emission, as shown in FIG. 2. The Jablonski diagram of FIG. 1 graphically illustrates vibrational levels of absorbance, non-radiative decay, and fluorescence. The traditional fluorescence processes become one branch in the new theory. A second branch of the new theory is called supracence because the emitted photons have more energy than those of absorbed photons, as graphically illustrated in FIG. 2. FIG. 2 illustrates the essence of supracence process, which considers a molecule as a dynamic cluster, constantly exchanging its quantum energy with molecular potential energy. The dotted line in FIGS. 1 and 2 is a reference energy level resembling that of the Fermi level. The significance of FIG. 2 is that it describes that photons emitted from a molecule (directly linked to $E_Q$) can have higher energy than those being absorbed by the same molecule in linear optics because the dynamic molecule may contribute some of its potential energy $E_P$ to the emitted photons. The scale of the orbital energy gap is exaggerated for clarity.

According to the inventors' discovery, the two types of energies within a molecule are constantly exchanging like a frictionless pendulum swinging back and forth. The first type energy is quantum energy ($E_Q$) gained by forming chemical bonds and it is clearly defined by the collective eigenvalues of the occupied molecular orbitals. The second type of energy is new and it describes the molecular potential ($E_P$) built into the dynamic cluster when the atoms in the molecule move relatively to each other. The definition of molecular potential energy is given by Equations 1 and 2 by summing over all bonds (N). Both energies are functions of molecular motions ($\Delta r$); their summation gives the total energy of the molecule ($E_T$) that stays constant at a given temperature, Equation 3.

$$E_P = \sum_{i=1}^{N} \int_{\lambda_0}^{\lambda} F_i dr_i \qquad (1)$$

where $F_i$ is bonding force and the ith bond or "the chemical bond" expressed as a function of bond-length variations ($\Delta r$) in Equation 2.

$$F_i = F_{i0} + \alpha_i \Delta r_i + \beta_i \Delta r_i^2 + \gamma_i \Delta r_i^3 \qquad (2)$$

and $$E_T = E_Q + E_P \qquad (3)$$

Figure 4:
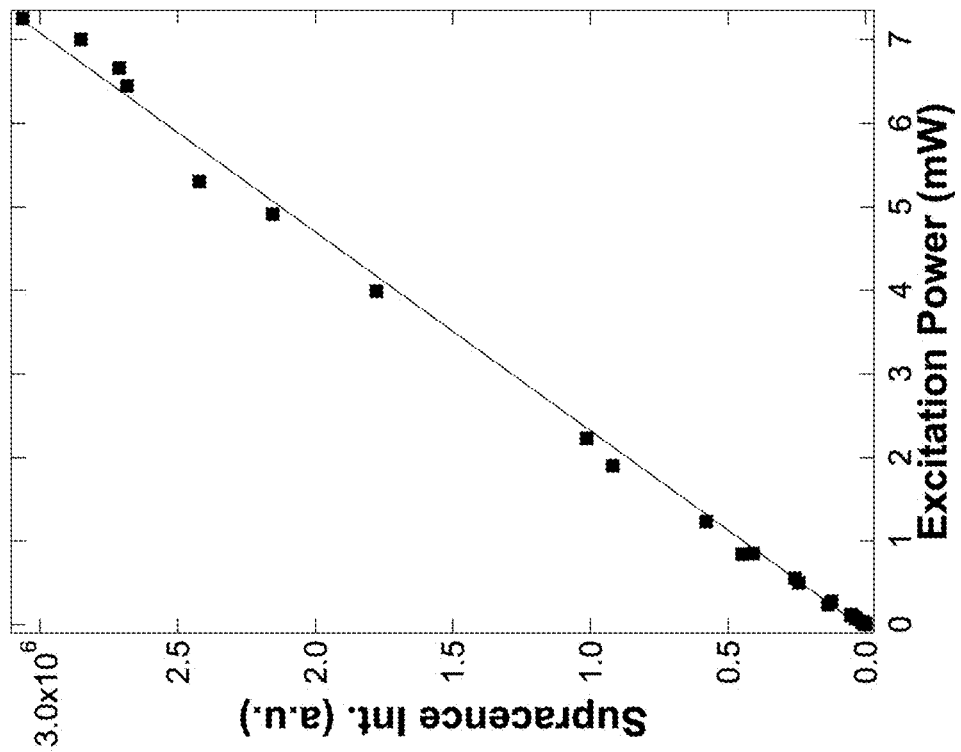
FIGS. 3 and 4 are graphs of experimental results that reveal the supracence intensity scales linearly with the excitation power.
Figure 3:
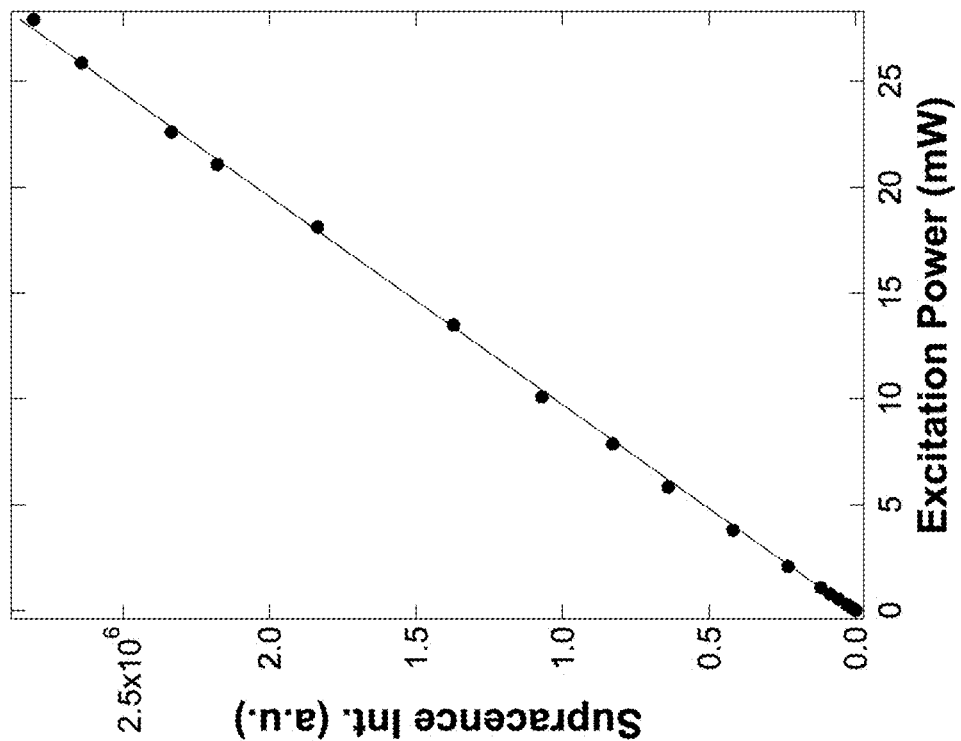

Under the current scope of molecular principles, only nonlinear optical processes can result in a photon with higher energy than that of it absorbed. Thus the critical experiments are to determine whether supracence is a linear optical process or a nonlinear optical process. FIGS. 3 and 4 reveal the supracence intensity scales linearly with the excitation power, thus proving supracence is a linear optic process. The supracence process described in the diagram of FIG. 2 absorbs one photon and emits one photon. For typical organic dyes like Rhodamine dyes, Boltzmann distribution points out that 99.9% of the population will occupy the lowest vibrational level (v=0) of the electronic ground state ($S_o$) at room temperature (T=298.2 K). Thus thermal energy cannot directly contribute to supracence excitation. Postulating photonic energy to populate higher vibrational levels (e.g., v=1) of the electronic ground state ($S_o$) leads to a two-photon excitation, contrary to the experimental results shown in FIGS. 3 and 4. Thus, supracence absorption must occur when molecular potential energy ($E_P$) drives the absorption gap low enough to match the energy of incoming photons. This supracence absorption mechanism is validated as a one-photon absorption process. Moreover, the linearity of the supracence intensity versus excitation power indicates that the extra energy gained in supracence must come from the molecule itself—the potential energy.

To further support work with supracence, new spectrometers were built to measure spectral properties of supracence and new microscopes were set up to image molecular phenomena of supracence. First, we define supracence efficiency $\Psi(\lambda)$ at a given wavelength $\lambda_0$ as the product of absorptivity $\varepsilon(\lambda)$ and integrated supracence intensity energetically above the excitation line $\lambda$ up to the appearance of supracence ($\lambda$) at high-energy onset, Equation 4. Supracence efficiency importantly reports how efficient each excitation wavelength can channel its excitation energy through the molecule to emerge as supracence photons.

$$\Psi(\lambda) = \varepsilon(\lambda) \int_{\lambda_0}^{\lambda} S(\lambda) d\lambda \qquad (4)$$

where $S(\lambda)$ is the spectrum of supracence at a particular excitation wavelength.

Figure 5:
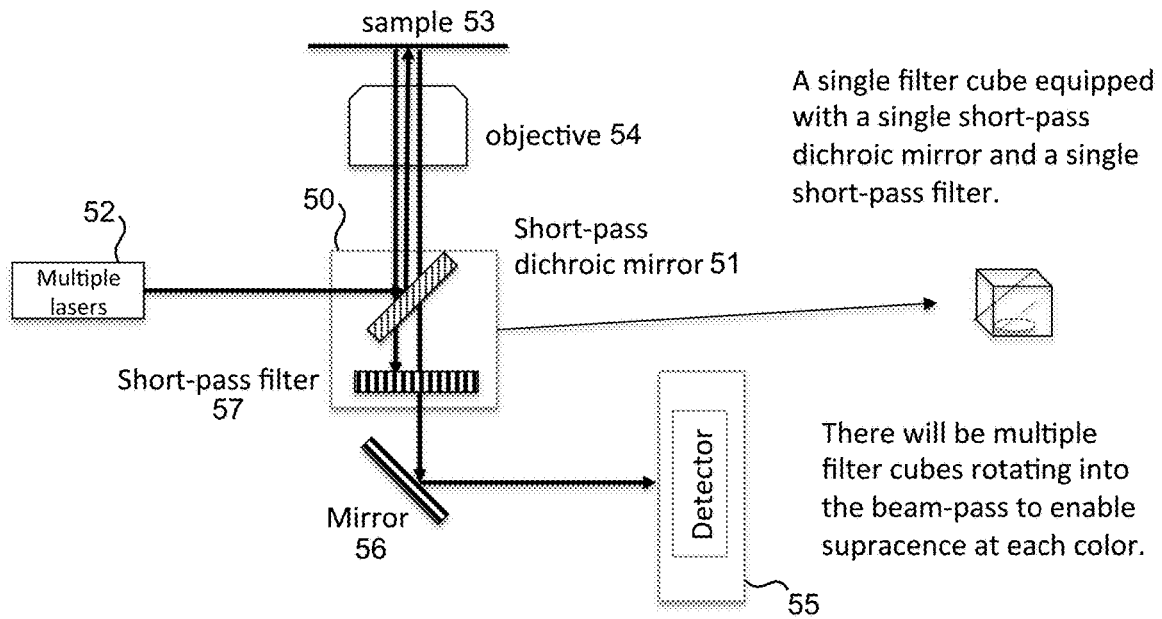
FIG. 5 is schematic diagram illustrating a new microscope to image molecular phenomena of supracence.

To capture the strength of supracence, several versions of supracence microscopes can be designed and manufactured. The first version shown in FIG. 5 is to perform a single supracence measurement using a set of optics in a single microscope cube 50. The cube is equipped with a single-edge, short-pass dichroic mirror 51 to reflect the laser 52 to the sample 53 via objective lens 54. Both fluorescence and supracence can be excited by this laser. Because the fluorescence has long wavelengths, most fluorescence photons are blocked by the short-pass dichroic mirror 51, but some can pass through. Those few fluorescence photons that do pass through are eliminated by the short-pass filter 57 that typically reduces fluorescence intensity by six orders of magnitude. Only supracence can maximally pass through both the short-pass dichroic mirror and the short-pass filter and subsequently imaged on the CCD camera 55 via mirror 56.

The strength of this design is that only supracence is measured because fluorescence is blocked by the combination of the short-pass dichroic mirror and the short-pass filter. The design aims to maximize the supracence sensitivity of a single type of molecules because the laser excitation, the short-pass dichroic mirror, and the short-pass filter are optimized for this molecule and optimum supracence or desired spectral region can be selected.

This design requires each laser has its own filter cube consisting a set of optics for both excitation and measurement of supracence imparted by this laser. Thus multiple filter cubes are needed for multiple lasers and the corresponding supracence imaging. Because rotating each filter cube into beam position will take time on the scale of seconds, there is a time shift between each supracence imaging by different lasers. This design captures the optimum excitation wavelength matching to the molecular supracence properties and filter cube optics—both the short-pass dichroic mirror and the short-pass filter. No fluorescence properties are being studied in this version of microscope design.

Figure 6:
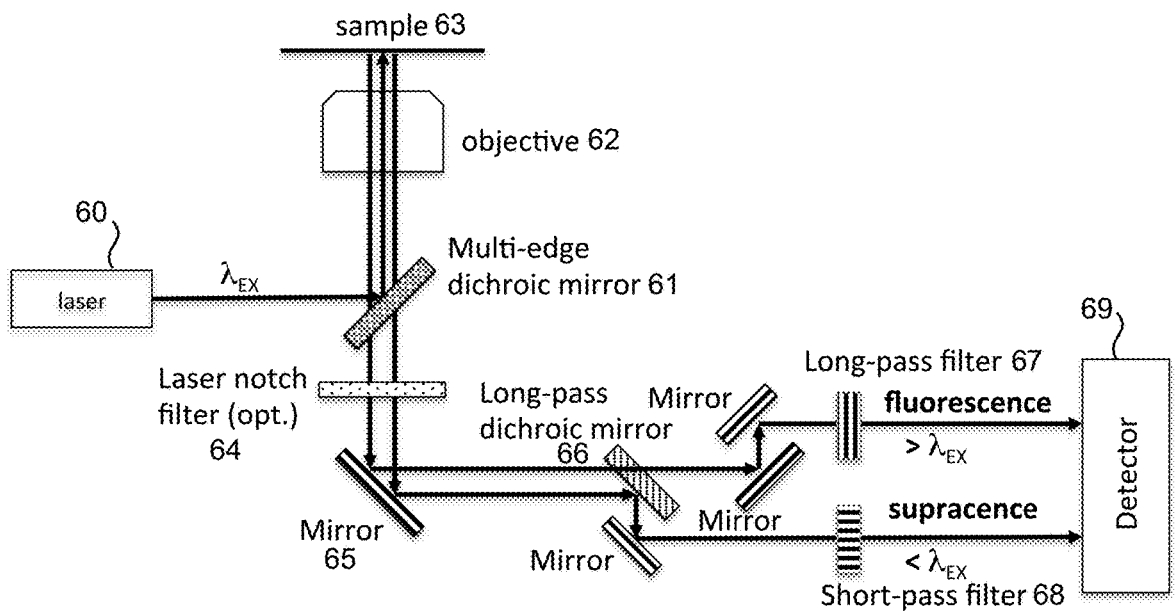
FIG. 6 is a schematic diagram illustrating a new microscope to image both fluorescence and supracence.

The second supracence microscope design shown in FIG. 6 aims to capture both fluorescence and supracence simultaneously, so that their mutual exclusion principle and complementarity principle can be explored. When fluorescence imaging is applied, in fact only part of molecular behavior is measured because molecular behavior in supracence is ignored. In supracence imaging, conversely, the fluorescence molecular behavior is neglected. Thus measuring both fluorescence and supracence is optimal approach because the measurement envelope the total emission phenomena.

Laser 60 emits an excitation wavelength of $\lambda_{EX}$ which is reflected by multi-edge dichroic mirror 61 and focused by objective lens 62 on a sample 63. The reflected light passes through the objective lens 62 and through multi-edge dichroic mirror 61 and optional laser notch filter 64. The light is then reflected by mirror 65 and, depending on the emitted wavelength of the light from the sample, the light is split by long-pass dichroic mirror 66. For fluorescence, $>\lambda_{EX}$, the light passes through the long-pass dichroic mirror 66 and reflected by a pair of mirrors to pass though a long-pass filter 67 as fluorescence. For supracence, $<\lambda_{EX}$, the light is reflected by a mirror to pass through a short-pass filter 68. The CCD camera 69 responds to both fluorescence and supracence.

A key advantage of this design is that one can tune the probability of supracence and fluorescence. Fluorescence produces hot emitters because each excitation the out-going photons carry less energy than the in-coming photons. Supracence, however, siphons energy away from the molecules and thus produces cold emitters. In bioimaging and living cell imaging, there has been a persistent problem of photo-toxicity. In other words, fluorescence excitation has constantly deposited energy into living tissues or cells that produces disturbing stress on such living systems. Frequently, living cells are killed by such photo-toxicity when the stress becomes so prevalent and passes the point of no return. Simultaneous supracence and fluorescence imaging can manage the energy balance and one can achieve energy-neutral homeostasis, in which the energy deposited by fluorescence is mostly removed by energy siphoning of supracence. Such microscopes are expected to set the standard of future biological imaging because the photon-perturbation to the biosystems being studied are minimal; thus, unlike current fluorescence imaging, more physiologically relevant phenomena will be truly revealed.

For example, Rhodamine B is a highly efficient fluorophore and frequently used to label biomolecules in living cells. When Rhodamine B in living cells is imaged using a blue (e.g., 488-nm Ar laser) or green laser (e.g., 532-nm laser), molecular emission will be dominantly fluorescence. Hardly any supracence can be produced. In these examples, the extra energy between absorption and emission photons will eventually be deposited into the cells as heat, thus causing photo-toxicity. When experimental setup, however, capitalizes supracence property by exciting Rhodamine B away from its equilibrium structure, Rhodamine B will be strongly emitting both fluorescence and supracence. Using a 561-nm excitation laser, a single Rhodamine B dye will have 47.5% probability of supracence and 52.5% of fluorescence. The supracence emission will cool the dye and fluorescence emission will heat up the dye; a delicate balance between heating and cooling will produce minimal stress to the living cells and thus physiological behavior more close to natural biology or true disease mechanisms can be observed. Contrasting to using short wavelength lasers (488 nm or 532 nm), which mostly will heat up the cells and cause physical damage or alteration of gene expressions (e.g., producing heat-shock proteins), the long wavelength laser (561 nm) will impart both cooling and heating effects from supracence and fluorescence, respectively, thus minimizing or nearly eliminating photo-toxicity in live cell imaging.

Blocking the laser excitation line only, proper chosen multi-edge dichroic mirror will allow both fluorescence and supracence to pass through. The supracence and fluorescence are separated by a long-pass dichroic mirror and residue laser intensities are further removed by long-pass filter and short-pass filter in corresponding channels, respectively. Finally, supracence and fluorescence can be imaged on a single CCD chip or alternatively two synchronized cameras can capture them individually.

Fluorescence imaging measures the long-tail end of the emission spectrum, and emissions corresponding to decaying to higher vibrational levels of the ground electronic states. Thus typical fluorescence covers about 100-nm width of the spectrum. Supracence imaging, however, measures the sharp and high-energy end of the emission spectrum and emission to higher vibrational levels does not gain enough energy to appear in supracence. Hence supracence imaging only measures the zero-to-zero vibronic transition, resulting in ultra-sharp peaks. Taking advantage of these properties, supracence microscope can achieve unprecedented spectral resolution, which more than double the capacity of state-of-art fluorescence imaging.

Figure 7:
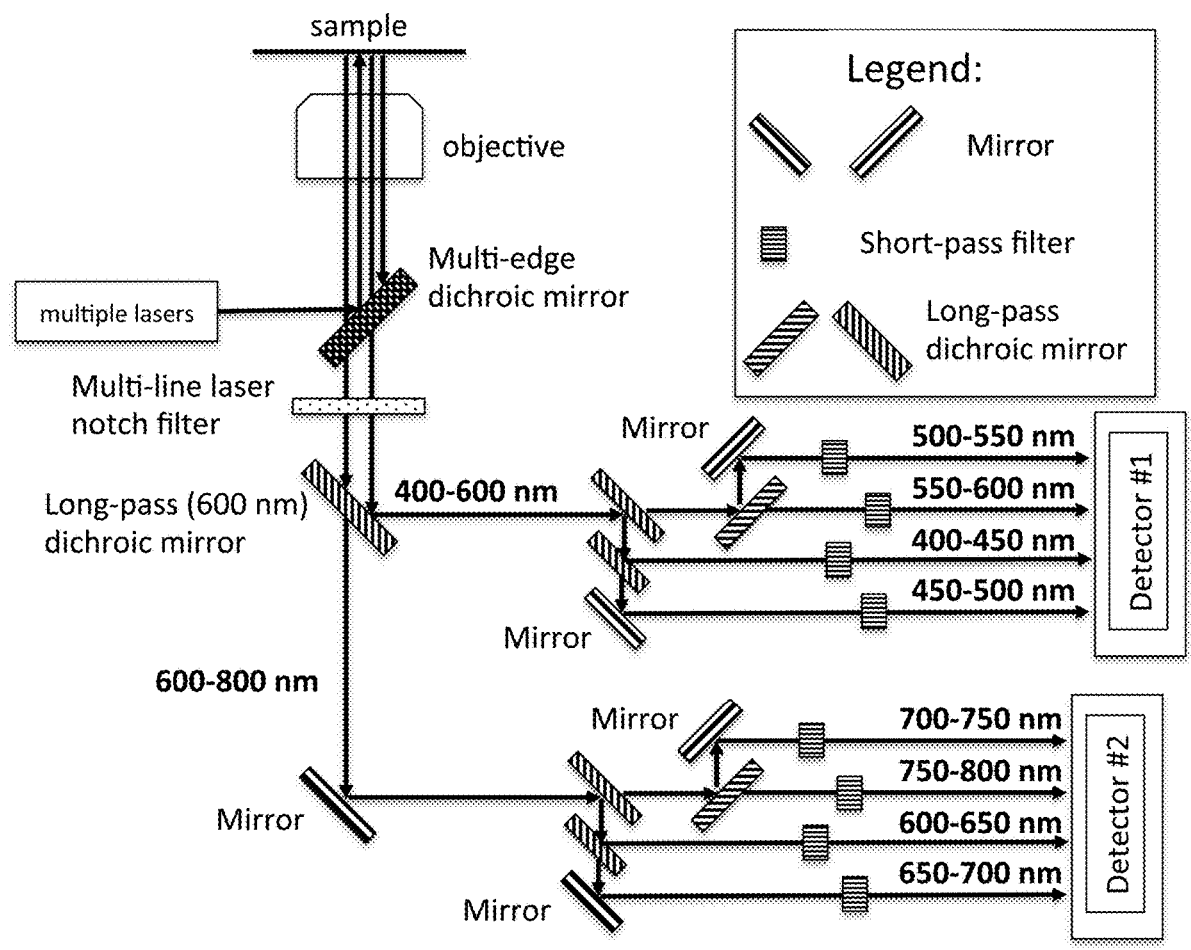
FIG. 7 is a schematic diagram illustrating a new microscope to simultaneously measure eight colors of supracence.

The supracence microscope shown in FIG. 7 is a modification of the basic microscope shown in FIG. 6. This version has unprecedented spectral resolution. Unlike fluorescence whose band covers 100-width of spectra, supracence band is narrower and the selection of proper short-pass band filter can further contract supracence bands into slender peaks. Thus supracence imaging can more than double the spectral capacity of fluorescence imaging. The additional advantage of this design is that it allows simultaneous imaging of both fluorescence and supracence. In the double quad-view setup, fluorescence may appear in different quadrants or even another camera.

The design of multi-color supracence microscope allows simultaneous measurements of fluorescence and supracence for each laser excitation. In this design, we show measuring eight colors of supracence using two CCD cameras, each camera using one of its four quadrants to measure one color. For example, a 555-nm laser will impart supracence in the 500-550-nm quadrant of CCD #1. At the same time, this laser will also excite fluorescence, which will be directed to 550-600-nm quadrant in CCD #1 and the 600-650-nm quadrant in CCD #2. The excitation laser 555-nm beam is removable by the combination of the multi-edge dichroic mirror and the multi-line laser notch filter; thus only supracence and fluorescence are able to pass through and arrive at the detectors.

The strength of multi-color supracence design is that supracence and fluorescence are measurable simultaneously at multi-colors. Although supracence at difference colors (e.g., 550-600 nm and 600-650 nm) cannot be measured simultaneously because of fluorescence interference, excitation lasers can fire quite fast at millisecond level or less; thus nearly simultaneous imaging of difference supracence colors can also be obtained.

Measuring more colors in a single sample is important because fluorescence imaging is presently the method of choice in the studies of both healthy and disease-causing cells. However, the limitation of four colors makes it impossible to study the relationships of larger number of biomolecules. Many biological molecular assemblies, such as ligand-receptor-signaling complexes and biological molecular machines, have more than four components, thus it is difficult for fluorescence to decipher their working mechanisms. Supracence is superior in this regard and it enables the studies of eight colors with essentially little spectral overlaps. While using band pass filters, supracence imaging may even triple fluorescence resolution, thus allowing, e.g., monitoring 12-protein assemblies in living cells. These capabilities are important because the number of biomolecules that supracence can measure frequently appears in real-world biological assemblies. For example, the death-inducing signaling complex-α comprises of eight proteins and ultimately determines the life and death of the cell. Understanding their formation in live cells is vitally important for treating diseases like various cancers.

Figure 8:
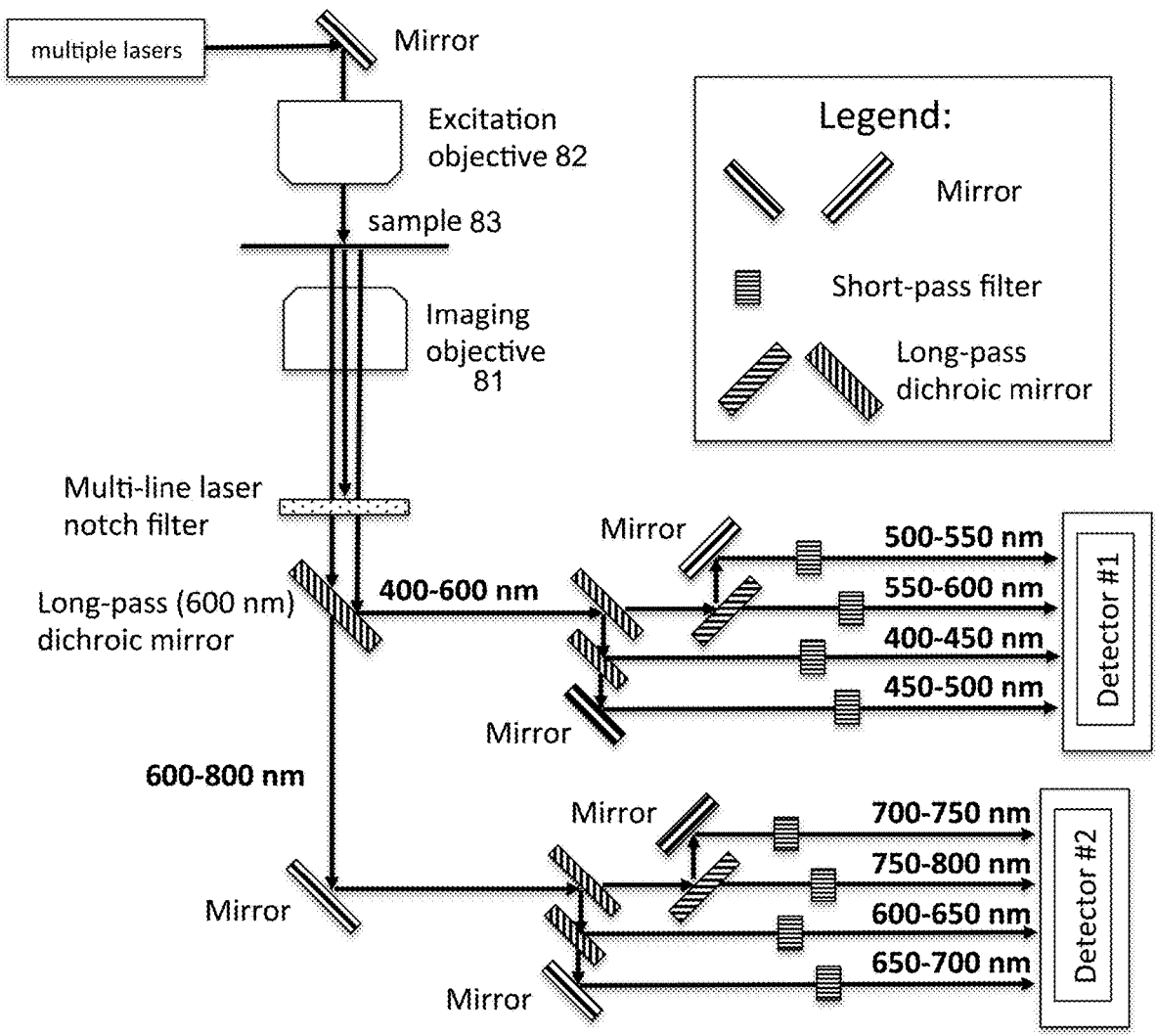
FIG. 8 is a schematic diagram illustrating a new microscope to simultaneously measure eight colors of supracence using a dual objective design.

FIG. 8 shows a modification of the microscope shown in FIG. 7 in which there is both an imaging objective lens 81, there is also an excitation objective lens 82 with the sample 83 placed between the two lenses. All three designs can introduce their lasers from a second objective in addition to the imaging objective. FIG. 8 illustrates this alternative design using the superior spectral resolution design shown in FIG. 7. This dual objective design can be easily applied to other configurations as well.

Figure 9A:
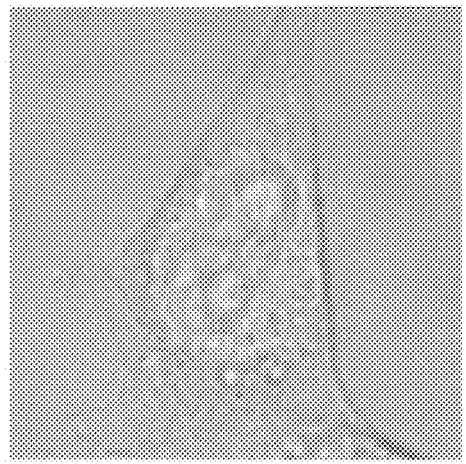
FIGS. 9A to 9D are images contrasting fluorescence and supracence obtained from live cells.
Figure 9B:
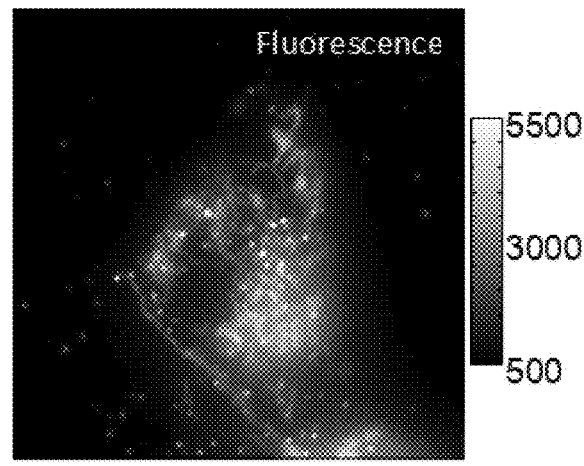
Figure 9C:
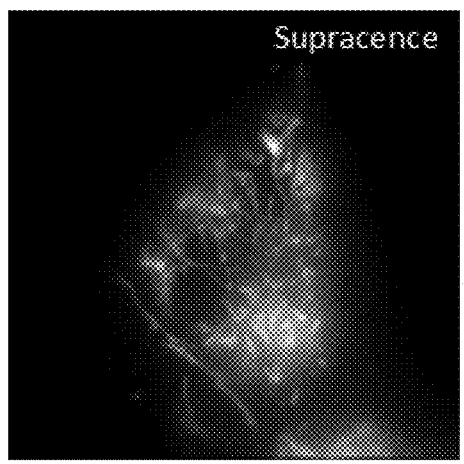
Figure 9D:
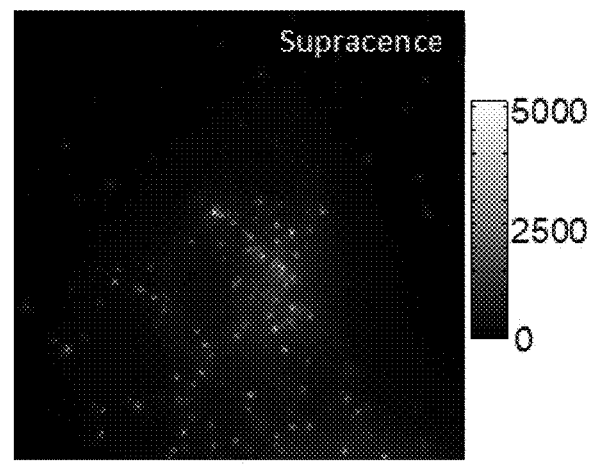

Unlike fluorescence, supracence completely resolves two emitters with separation of emission maximums of just 32 nm. FluoSpheres™ of 40 nm doped with Rhodamine B derivatives are used to label endosomes (endo) and lysosomes traveling on microtubules in live cells, as shown in FIG. 9A, while Rhodamine 123 is used to stain mitochondria (mito), some also moving on microtubules. Endosomes and lysosomes impart spotty patterns, whereas mitochondria yield worm-like patterns. Fluorescence imaging (excited by a 532-nm laser) cannot distinguish these two dyes and hence both spotty and worm-like patterns were observed, as shown FIG. 9B. Excited by the same 532-nm laser, supracence imaging specifically resolved the mitochondria, the worm like pattern, but did not detect any spotty pattern, as shown in FIG. 9C. Similarly, supracence excited by a 561-nm laser selectively revealed the spotty pattern of endosomes and lysosomes, but the worm-like pattern of mitochondria was not detected, as shown in FIG. 9D. These results demonstrate that fluorescence imaging of mitochondria has more than 200% crosstalk and fluorescence imaging of endosomes yields ~50% crosstalk. However, supracence imaging of mitochondria and endosomes has near zero crosstalk.

Both excitation selectivity and spectral narrow emission enable very efficient wavelength multiplexing for supracence imaging. To demonstrate these two key points, Rhodamine 123 was selected to stain mitochondria and Rhodamine B derivative in FluoSpheres™ to label endosomes/lysosomes in live cells (FIG. 9A). The mitochondria impart worm-like pattern, whereas endosomes/lysosomes yield sharp spots; these two distinct patterns are chosen because they can be easily recognized. When excited by 532-nm laser, both Rhodamine B and Rhodamine 123 fluoresce and the resulting image reveals both sharp spots of endosomes/lysosomes and worm-like pattern of mitochondria (FIG. 9B). The reasons are two-fold: continuous fluorescence excitation is not selective and rather broad fluorescence emission has strong overlap in a large range of the spectra. However, when supracence is used to measure each probe, we obtained a clean image of mitochondria under 532-nm excitation (FIG. 9C) and another clean image of endosomes/lysosomes under 561-nm excitation (FIG. 9D). Of particular significance is that the supracence image of mitochondria has no measurable crosstalk or interference from endosomes/lysosomes. Similarly, measurements of endosomes/lysosomes have no mitochondrial contamination. These results prove that supracence is much more efficient at wavelength multiplexing and emitters with absorption or emission peaks only separated by 32 nm in the same sample can be effectively imaged individually.

Figure 10A:
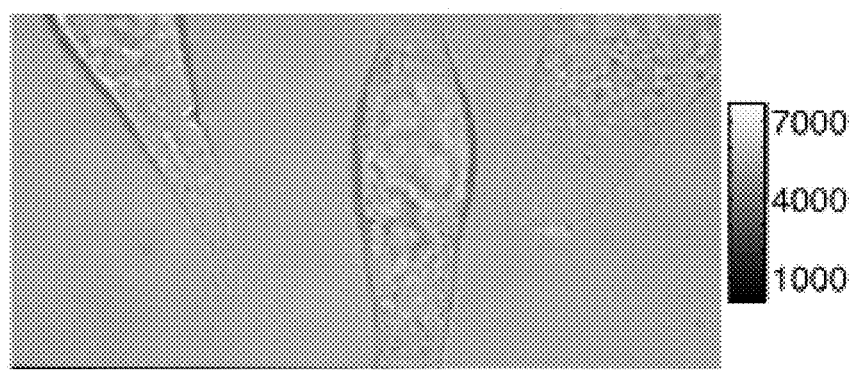
FIGS. 10A to 10D are images contrasting fluorescence and supracennce obtained from other example live cells.
Figure 10B:
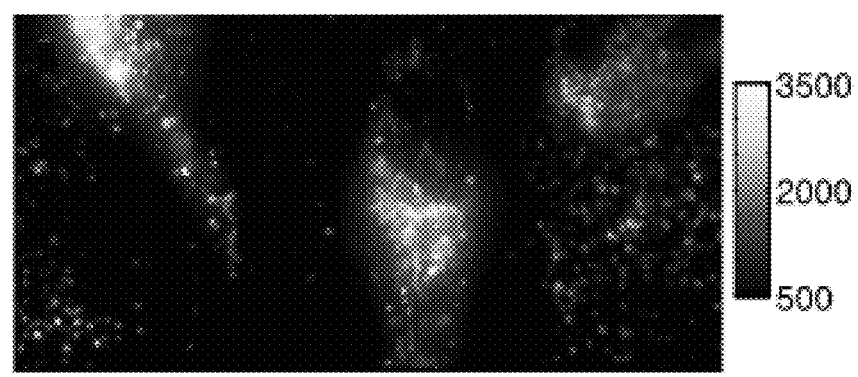
Figure 10C:
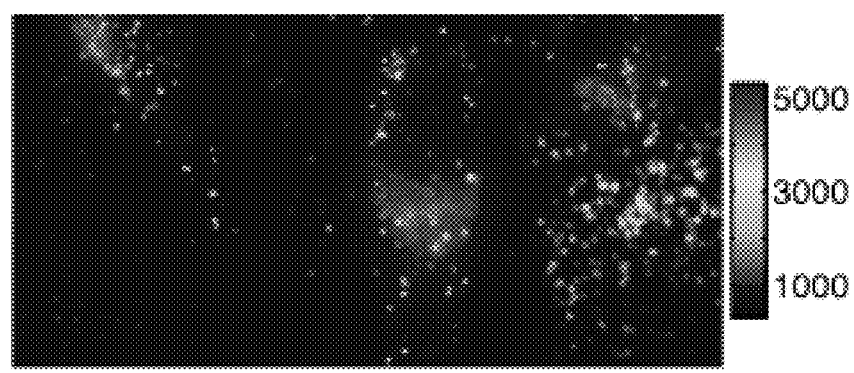
Figure 10D:
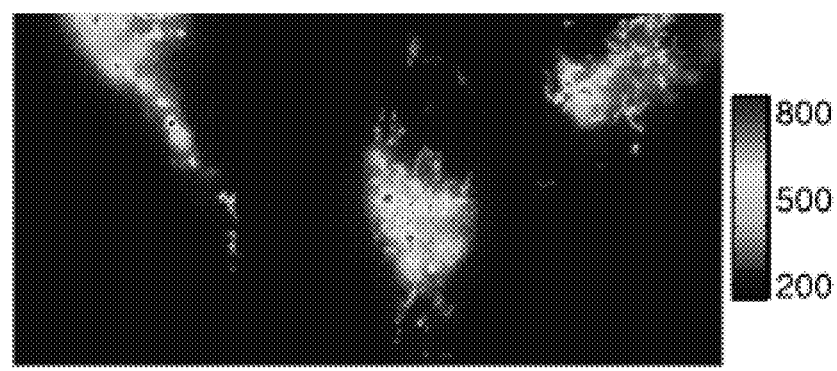

To further confirm the above conclusions, validations in three other living cells in FIG. 10A were sought. These living cells had endocytosed FluoSpheres™ containing Rhodamine B derivative and their mitochondria were stained using membrane-permeable Rhodamine 123 dye. Again, fluorescence imaging reveals both the spotty pattern of endosomes/lysosomes and the worm-like pattern of mitochondria, resulting in an unresolved image of both organelles (FIG. 10B). Supracence imaging using a 561-nm laser on the same sample, however, specifically divulged the endosomes/lysosomes nanospheres only (FIG. 10C). There are two classes of nanospheres in the image: some stationary nanospheres were chemically adsorbed to the bottom of lysine-coated dish through charge interactions, while others were endocytosed by the living cells, which were actively transporting the nanoparticles on the microtubules. Similarly, supracence imaging of mitochondria using a 532-nm laser on the same sample unveiled the actively worm-like motions of mitochondria (FIG. 10D). In the supracence imaging of mitochondria, the nanospheres were clearly not present, as evidenced by the areas outside of the live cells at bottom left and right of FIG. 10D. Conversely, in the supracence imaging of endosomes/lysosomes, no worm-like mitochondrial patterns were detected (FIG. 10C). Thus supracence is not only effective at spectral multiplexing because of superior spectral resolution, but also impart high-quality individual images without cross contamination.

Currently, wavelength multiplexing allows fluorescence detections up to four fluorophores within the visible and near IR spectrum, roughly from 450 nm to 850 nm with considerable crosstalk. For example, the instrumental cyanine dyes such as Cy3, Cy5, and Cy7 have fluorescence bands covering from 550 nm to 850 nm with above 10% spectral overlaps between adjacent dyes. Similarly, only two Rhodamine dyes from 500 nm to 700 nm, and three BODIPY dyes from 500 nm to 750 nm can be selected with <10% spectral overlaps. Supracence, however, should enable detections up to ten fluorophores in the spectral width from 450 nm to 850 nm with no measurable crosstalk based on high spectral resolution of supracence work presented here. Thus, this superior capability more than doubles the current wavelength multiplexing capabilities. This tremendous advancement in spectral multiplexing originates from the rather narrow supracence band coupled with ultra sharp selectivity of supracence excitation. The origin of such sharp supracence bands and excitation selectivity is in turn controlled by the limited molecular dynamics to drive the molecule along the direction to emit higher energetic photons. These breakthrough technologies described here will greatly augment capability in both spectroscopic measurements and molecular imaging.

Figure 11:
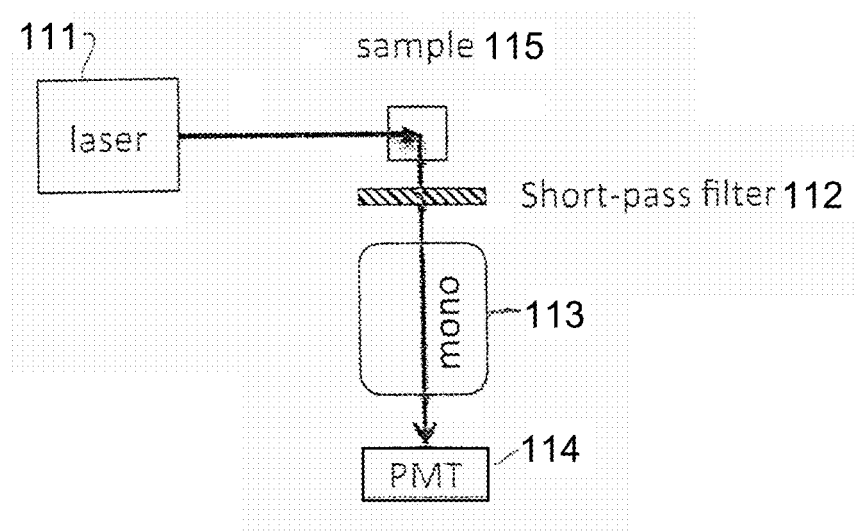
FIG. 11 is a schematic diagram illustrating a new spectrometer to measure spectral properties of supracence.

Supracence spectra were measured using a spectrometer as shown in FIG. 11. The excitation source 111 is a 561-nm laser or 532-nm laser for FluoSpheres™ (manufactured by ThermoFisher Scientific) or Rhodamine 123, respectively. The excitation energy is attenuated using neutral density filters (not shown) and typically limited to <1 mW at the sample chamber. The supracence was selected using an ultra-sharp short-pass filter 112 connected to a one-inch lens tube to exclude other stray light. The supracence was then further attenuated using two 10% neutral density filters (not shown) to reduce the light intensity for the detector. After attenuation, supracence was focused onto the entrance slit of the monochromator 113, to which a highly sensitive PMT (photomultiplier tube) detector 114 is connected to the opposite end. Scanning the monochromator 114 while exciting the sample 115 with the laser beam yields the desired supracence spectrum. A typical sample 115 in cuvette is excited using the laser 51. The supracence from the sample 115 is cleaned up using a 6-OD ultra-sharp short-pass filter 52 to allow the spectral wavelength below laser excitation line to pass through. The supracence is then dispersed in a monochromator 113 to spectrally resolve the supracence intensity at each wavelength. For strong supracence intensity, neutral density filters were inserted in the optical path to avoid saturation of the PMT detector 114. Typical absorption spectra were collected using a Varian Cary 1C instrument and fluorescence spectra were collected using a SPEX Fluorolog-3-21 in standard solution such as water for FluoSpheres™ and ethanol for Rhodamine 123.

Because supracence is distinct from other spectroscopies, several different designs are required to capture its advantage. The first design is based on low-cost single point photo detectors (PD) such as photoconductive detectors, photovoltaic detectors, and photoemissive detectors. Specific PD examples include photomulitiplier tube (PMT), phototransistor, complementary metal-oxide-semiconductor (CMOS), charge coupled device (CCD), Photodiode or avalanche photodiode (APD).

Figure 12:
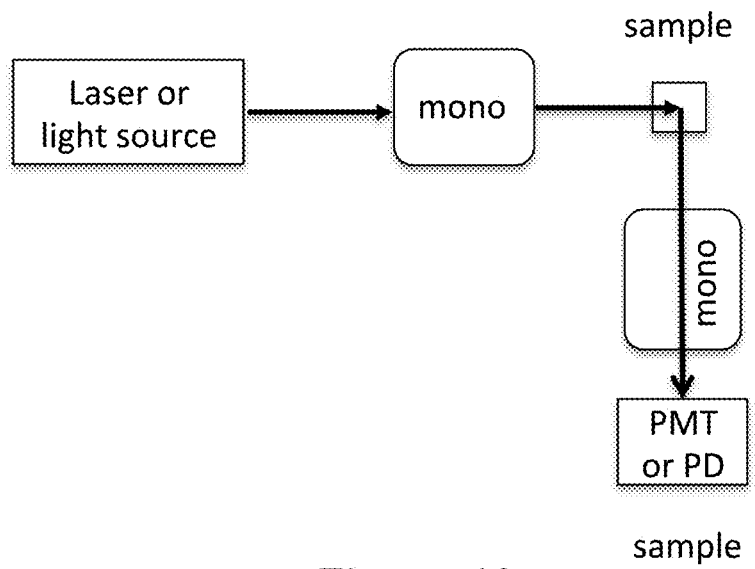
FIG. 12 is a schematic diagram illustrating a supracence spectrometer which employs two monochromators, one for selecting the wavelength of excitation and one for measuring the spectrum of supracence.

The simplest supracence spectrometer will employ two monochromators, one for selecting the wavelength of excitation and one for measuring the spectrum of supracence (FIG. 12). This type of supracence spectrometers is ideal for measuring a single supracence spectrum at a fixed excitation wavelength. When supracence spectra at many excitation wavelengths are needed, the excitation monochromator must also scan the required spectral region. This creates a double scanning situation, which can be completed easily using the double-scan configuration, albeit at a slower speed.

Figure 13:
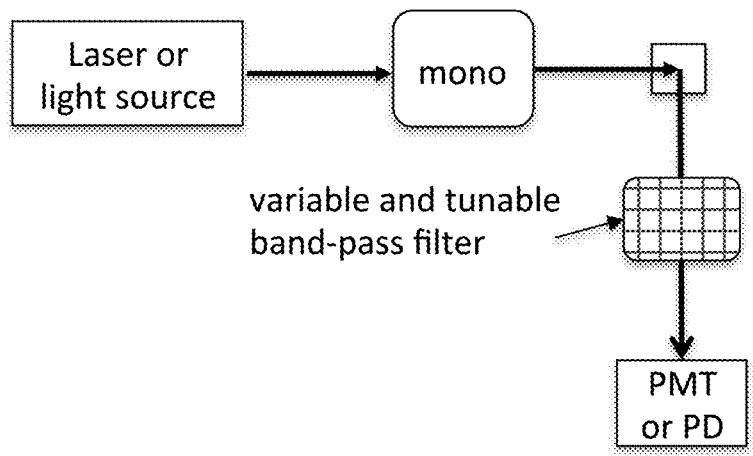
FIG. 13 is a schematic diagram illustrating a supracence spectrometer which uses variable and tunable band-pass filter to replace the emission monochromator of FIG. 12.

To address the low data acquisition rate of the double scanning configuration, a faster design shown in FIG. 13 uses variable and tunable band-pass filter to replace the emission monochromator. The band-pass filter with desired tunable spectral width measures all supracence photons at once. Thus, this configuration reduces double scanning to single scanning for obtaining a total integrated supracence spectrum for each excitation wavelength. Scanning through desired excitation wavelength yields a spectrum of the total integrated supracence, whose maximum peak is characteristic to its corresponding compound.

Figure 14:
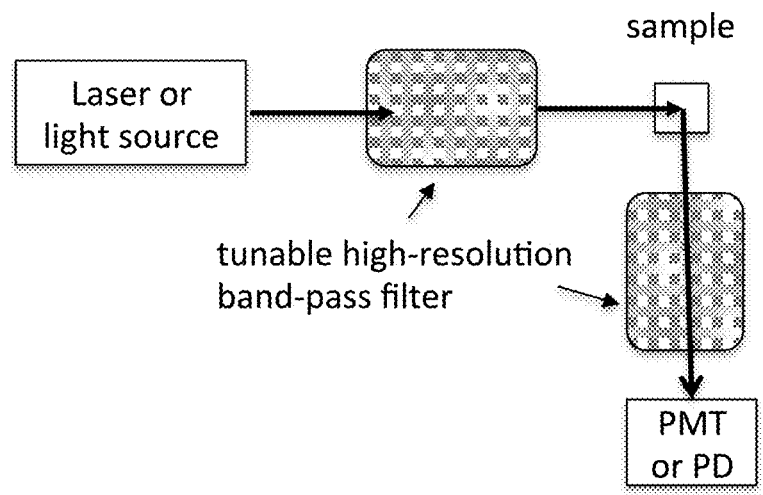
FIG. 14 is a schematic diagram illustrating a supracence spectrometer which uses high-resolution band-bass filters in place of the monochromators of FIG. 12.

The design of a supracence spectrometer can be based on a single-point detector, such as a photomultiplier tube (PMT) or other point detector, as shown in FIG. 14. These designs take advantage of the spectral resolution from monochromator (≤1-10 nm) to high-resolution band filter (1-3 nm), and then to variable band filter (10-100 nm). Because high-resolution band-pass filters are raveling the resolution of monochromator, supracence spectrometer can benefit from using high-resolution band-pass filters (FIG. 14). Although these three spectrometer-configurations illustrate the usage of monochromator, high-resolution band-pass filter and variable band-pass filter, they can be readily exchanged from one to the other to optimize for a particular measurement.

Figure 15:
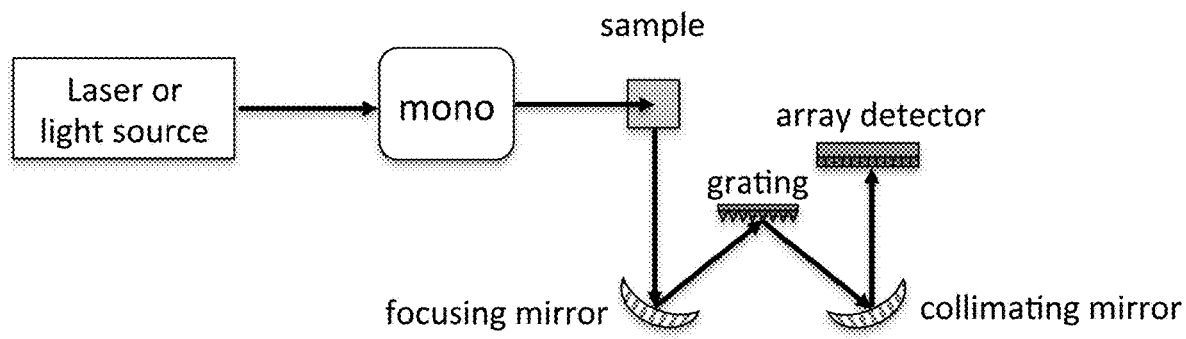
FIG. 15 is a schematic diagram illustrating a supracence spectrometer in which the excitation wavelength is selected using a monochromator and an array detector to reduce double scans.
Figure 16:
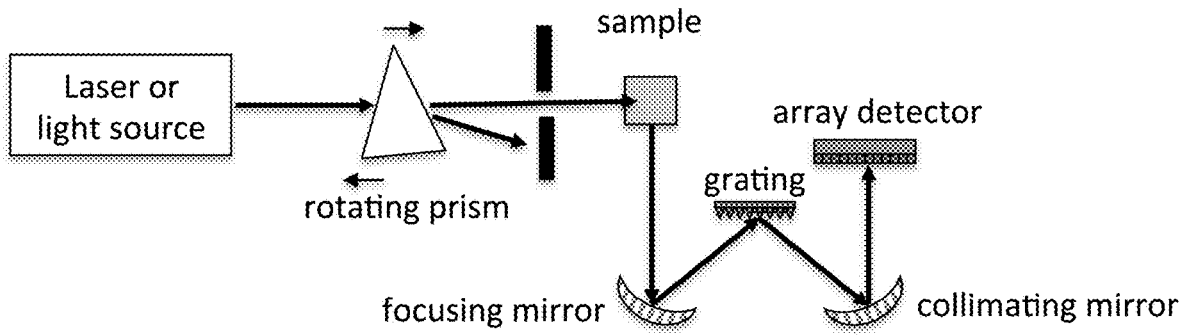
FIG. 16 is a schematic diagram illustrating a supracence spectrometer in which the excitation wavelength is selected using a prism and an array detector to reduce double scans.

The second design of supracence spectrometers use a grating to reduce double scans to a single scan, but they still resolve each individual supracence spectrum when array detectors are employed. Examples of such array detectors include linear CCD, linear CMOS, or diode array. The advantages of using array detectors are data can be acquired much faster down to millisecond regions and intensities are resolved at their specific wavelength. The excitation wavelength can be selected using either monochromator, as shown in FIG. 15, or high-resolution band filter or a prism, as shown in FIG. 16. For total integrated supracence intensities, no emission spectral resolution is required and the total supracence photons can be collected using a single-point detector like PMT or APD (avalanche photo-diode).

The peak or maximum wavelength of the total integrated supracence intensities is characteristic to the compound being detected and thus can be used to index or identify the compound, because the origin of supracence intensity comes from a unique combination of absorption properties and emission characteristics as well as its Stoke shift.

Figure 17:
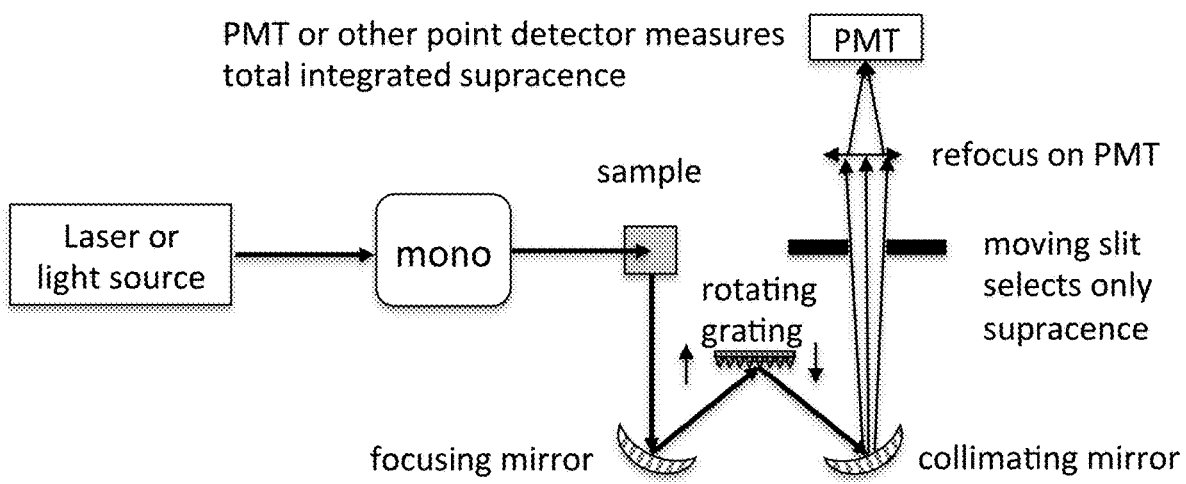
FIG. 17 is a schematic diagram illustrating a supracence spectrometer in which a moving slit selects only supracence and uses a photomultiplier tube or other point detector to measure total integrated supracence.

These supracence spectrometers use a grating and/or array detectors. Array detectors speed up the data collection rate because a whole supracence spectrum can be measured in one shot with refresh rate as high as several milliseconds (FIGS. 15 and 16). When supracence spectral resolution is not required, a single point detector like PMT (FIG. 17) can be used to collect all supracence photons at different wavelengths simultaneously.

Both UV-vis and fluorescence spectrometers are not capable of identifying a compound in the presence of other compounds because they produce broad and typical multiple bands whose origins are difficult to decipher. Overlapping of broad bands makes it nearly impossible to identify a specific compound and indeed UV-vis and fluorescence are not used to identify compound. Supracence, however, offers a single narrow band for each compound and its maximum peak wavelength is characteristic for the compound; thus it can identify each compound in a mixture, sparing the processes of tedious separations.

Figure 18:
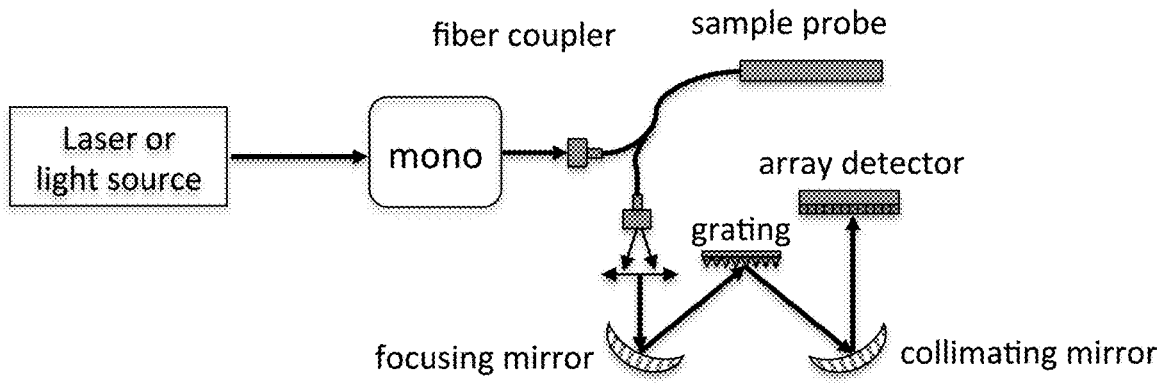
FIG. 18 is a schematic diagram illustrating a supracence spectrometer similar to FIG. 15 but uses fiber optic to direct excitation light to a sample and emission light to an array detector.
Figure 19:
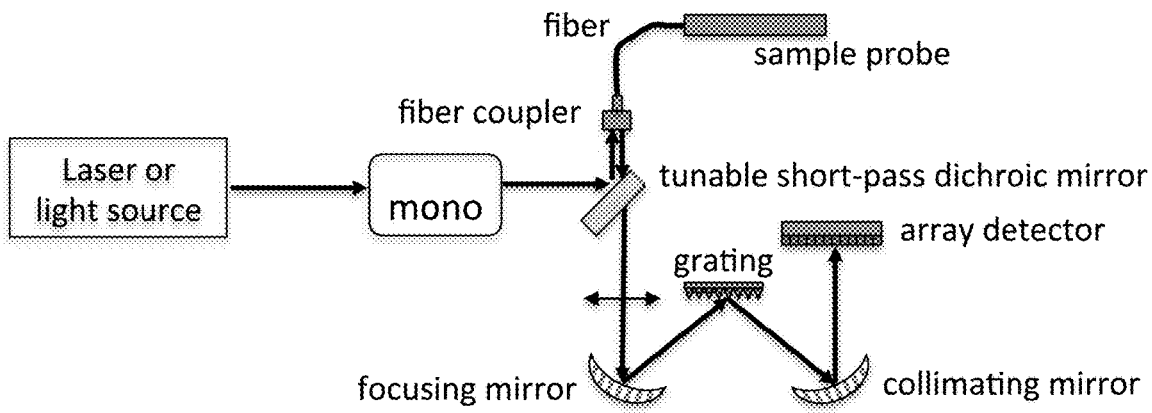
FIG. 19 is a schematic diagram illustrating a supracence spectrometer similar to FIG. 18 but uses a tunable short-pass dichroic mirror to direct emission light to the array detector.
Figure 20:
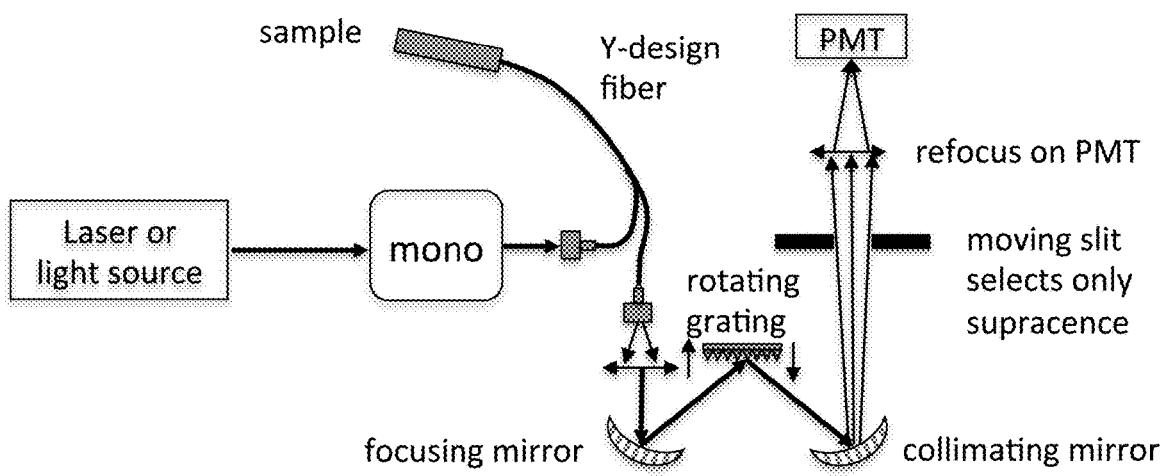
FIG. 20 is a schematic diagram illustrating a supracence spectrometer similar to FIG. 17 but uses fiber optic to direct excitation light to a sample and emission light to an array detector.

Supracence can be applied in pharmaceutical, clinical diagnosis, biotechnology, chemical, environmental, agricultural, semiconductor, food & beverage industries. In many situations like diagnosis of a tumor in the body or a virus infection of the plant, molecular separation is not an option. These are situations where a fiber-based supracence device shines, as shown in FIGS. 18 to 20. Because a fiber probe can reach the specific target and supracence can identify the molecular marker, fiber-based supracence spectrometer will have huge impact to above-mentioned industries.

An advantage of fiber-based Supracence spectrometers is that the fiber probe of the supracence spectrometer can be strategically placed at many targets such as inside human body, on the leaf of a plant, or on a production line. Its ability to identify specific compounds will offer invaluable information about diagnosis of diseases, monitoring of crop growth, and quality control in manufacturing.

In addition to UV-vis and fluorescence billion-dollar markets, flow cytometry market size is valued at about $4 billion in 2018. This is because there are critical needs to specify cells and thus their functions similar to correlating molecular structures to molecular properties. To determine complex phenotypes of various cells, many colors of signal channels are required. The bottleneck again occurs when fluorescence spectra produce broad and overlapping peaks when too many dyes are used to label cells. The whole visible spectrum can accommodate four dyes with reasonable spectral overlaps (~10%). This fact can be easily verified when one studies typical fluorescence spectrum like rhodamine B. However, to correctly analyze the phenotype of a cell, many more receptors or similar characteristics must be labeled and this is a task goes beyond the capability of fluorescence-based flow cytometry.

Figure 21:
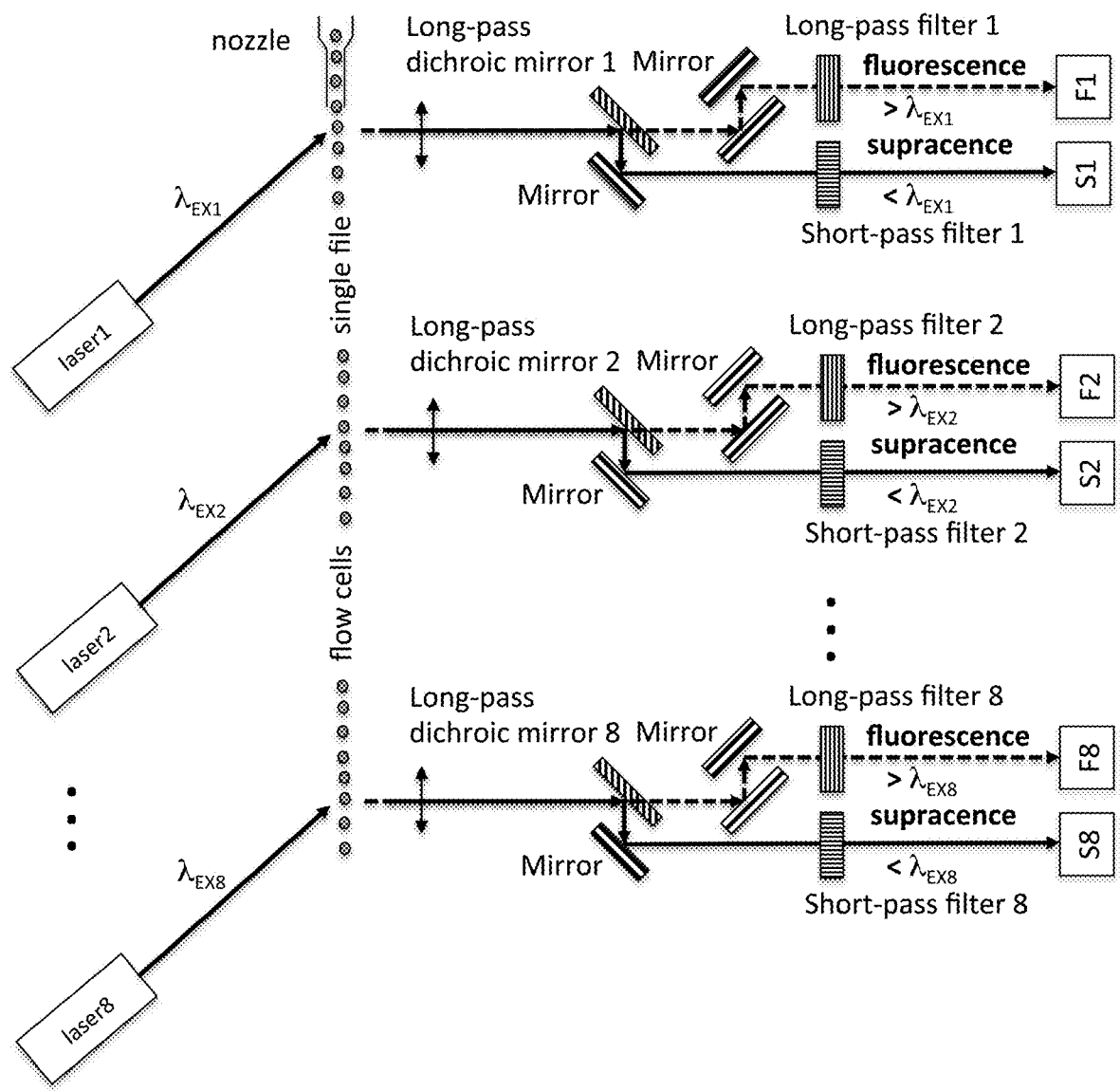
FIG. 21 is a schematic diagram illustrating a system for supracence flow cytometry in which multiple lasers are used, each optimized for a particular color of supracence.

For supracence flow cytometry, the lasers in FIG. 21 are constantly on to resolve both fluorescence and supracence simultaneously for each laser. This design arranges the laser focus spots into a single file like that of the flow cells. Each laser is optimized for a particular color, thus producing strong integrated supracence for each dye. The ratio or balance between supracence and fluorescence is experimentally determined and hence any overlaps can be better calculated using sample data and standard calibrations.

Supracence produces much narrow bands and resolution of supracence bands can be further increased using appropriate band-pass filters. This allows supracence to easily measure 8 colors with nearly no overlap (~1%). When band-pass filters are used in supracence, supracence spectral resolution is estimated to triple that of fluorescence resolution. The expected results will resolve up to twelve colors and thus many complex phenotypes of isolated cells can be much better characterized using supracence flow cytometry.

The spectral overlaps among dyes are the biggest barrier in fluorescence-based flow cytometry analysis. In fluorescence flow cytometry, population resolution is decreased by the spread or overlap due to spillover from other dyes. Multi-colors fluorescence-based flow cytometry has more spillover, thus contributing to higher background and uncertain results. This overlap is not eliminated by compensation and thus strategies to minimize spillover are the ultimate concerns in fluorescence-based flow cytometry, even for four or fewer colors. Supracence flow cytometry can study more phenotypes, doubling or even tripling the number of biomolecules being labeled, with much improved accuracy because of narrow supracence bands and significantly reduced dye-dye overlaps.

While the invention has been described in terms of preferred embodiments, those skilled in the art will recognize that the invention can be practiced with modification within the spirit and scope of the appended claims.

Having thus described our invention, what we claim as new and desire to secure by Letters Patent is as follows:

1. An absorption-and-emission instrumental method, comprising the steps of:
  directing a light beam at a sample with an excitation wavelength of $\lambda_{EX}$ to excite the sample from a lowest electronic state and a lowest vibrational state to an excited state in a single step;
filtering spectra from the sample with imaging optics to separate wavelengths $<\lambda_{EX}$ from wavelengths $>\lambda_{EX}$; and
capturing the filtered spectra with wavelengths $<\lambda_{EX}$ with a detector to produce an output showing only supracence.

2. The method of claim 1, wherein the filtering step comprises selectively passing one or more wavelengths $<\lambda_{EX}$ and blocking all wavelengths $>\lambda_{EX}$.

3. The method of claim 1, further comprising the step of producing an image output from only the captured filtered spectra with wavelengths $<\lambda_{EX}$.

4. The method of claim 1, further comprising the step of capturing the filtered spectra with wavelengths $>\lambda_{EX}$ with a second detector or a second distinct region separate from the distinct region of the same detector that captures the filtered spectra with wavelengths $<\lambda_{EX}$.

5. The method of claim 4, further comprising the step of producing an image showing fluorescence using information from the second detector or separate distinct region of the same detector.

6. The method of claim 1, wherein the sample comprises a living cell.

7. The method of claim 6, wherein the sample comprises a cancer cell.

8. The method of claim 1, wherein the sample either has endogenous emitters or is labeled with fluorescent dyes.

9. The method of claim 1, wherein the sample is labeled with fluorescent nanoparticles or quantum dots.

10. The method of claim 1, wherein the sample comprises structures with non-zero supracence.

11. A microscope, comprising:
at least one light source for producing a light beam with an excitation wavelength $\lambda_{EX}$;
beam-forming optics for directing the light beam at a sample to excite the sample from a lowest electronic state and a lowest vibrational state to an excited state in a single step;
imaging optics configured to filter spectra from the sample to separate wavelengths $<\lambda_{EX}$ from wavelengths $>\lambda_{EX}$; and
at least one detector or distinct region thereof configured to capture only the filtered spectra with wavelengths $<\lambda_{EX}$.

12. The microscope of claim 11, further comprising one or more further detectors that capture the filtered spectra with wavelengths $<\lambda_{EX}$, the further detectors being configured to capture the filtered spectra with wavelengths $>\lambda_{EX}$.

13. The microscope of claim 11, wherein the beam-forming optics comprise a multi-edge dichroic mirror and an objective lens.

14. The microscope of claim 11, wherein the imaging optics comprise a short-pass dichroic mirror and a short-pass filter for blocking wavelengths $>\lambda_{EX}$.

15. The microscope of claim 14, wherein the short-pass filter is an ultra-sharp short pass filter connected to a lens tube to exclude stray light.

16. The microscope of claim 11, further comprising a filter cube for each respective light source, the filter cube being configured for excitation and measurement of supracence imparted by the respective light source.

17. A method of imaging with minimized photo-toxicity, comprising the steps of:
selecting a fluorophore with non-zero supracence for a given excitation wavelength $\lambda_{EX}$;
dying a sample with the selected fluophore; and
imaging the sample using only a laser with excitation wavelength $\lambda_{EX}$, and using simultaneous imaging of both fluorescence and supracence.

18. The method of claim 17, wherein the selecting step selects, from among a plurality of fluorophore options, the fluorophore with maximum supracence efficiency.

19. The method of claim 17, wherein the selected excitation wavelength $\lambda_{EX}$ is tuned and optimized to balance between fluorescence and supracence to lower stress to living cells.

20. The method of claim 17, wherein the fluorescence and supracence images are not optically separated while the sample is excited by the optimized excitation wavelength $\lambda_{EX}$ to reduce photo-toxicity.

21. A spectrometer, comprising:
at least one light source for producing a light beam;
first optics for selecting from the light beam an excitation wavelength of $\lambda_{EX}$ with which to expose a sample to excite the sample from a lowest electronic state and a lowest vibrational state to an excited state in a single step;
second optics for selecting a single supracence spectrum $<\lambda_{EX}$ from the sample;
one or more detectors configured to capture only the selected single supracence spectrum.

22. The spectrometer of claim 21, wherein the first and second optics comprise first and second monochromators respectively.

23. The spectrometer of claim 22, wherein the monochromators have spectral resolutions of $\leq 1$-$10$ nm.

24. The spectrometer of claim 21, wherein the first optics comprise a monochromator, and the second optics comprise a variable and tunable band-pass filter.

25. The spectrometer of claim 24, wherein the monochromator has a spectral resolution of $\leq 1$-$10$ nm, and the variable and tunable band-pass filter has a spectral resolution of 1-3 nm.

26. The spectrometer of claim 21, wherein the first and second optics comprise first and second tunable high-resolution band-pass filters respectively.

27. The spectrometer of claim 26, wherein the tunable high-resolution band-pass filters have spectral resolutions of 10-100 nm.

28. The spectrometer of claim 21, wherein the first optics comprises a monochromator, a prism, or a high-resolution band filter.

29. The spectrometer of claim 28, wherein the second optics comprise a grating, and the at least one detector is an array detector.

30. The spectrometer of claim 28, wherein the second optics comprise a rotating grating or mirror, and the at least one detector is a single-point detector.

31. The spectrometer of claim 21, further comprising a sample probe using optical fibers to couple to the first optics and the second optics.

32. The spectrometer of claim 31, wherein the fiber-optics sample probe uses a Y-configuration fiber to couple to the first optics and the second optics.

33. The spectrometer of claim 31, wherein a conditioned light beam after the first optics is launched into the optical fiber via a tunable short-pass dichroic mirror, while the second optics selects supracence passing through the tunable short-pass dichroic mirror onto the detector.

34. A flow cytometer, comprising:
n lasers with respective excitation wavelengths of $\lambda_{EX1}$ to $\lambda_{EXn}$, each laser being optimized for a particular color;

beam-forming optics configured to align laser focus spots of the n lasers on successive points of a single file flow cell line to excite samples from a lowest electronic state and a lowest vibrational state to an excited state in a single step;

for each excitation wavelength $\lambda_{EX_i}$ from $\lambda_{EX1}$ to $\lambda_{EX_n}$,
  imaging optics configured to filter spectra from the single file flow cell line to separate wavelengths $<\lambda_{EX_i}$ from wavelengths $>\lambda_{EX_i}$, and
  one or more detectors configured to capture only the filtered spectra with wavelengths $<\lambda_{EX_i}$.

35. The flow cytometer of claim 34, further comprising one or more further detectors that capture the filtered spectra with wavelengths $<\lambda_{EX_i}$, the further detectors being configured to capture the filtered spectra with wavelengths $>\lambda_{EX_i}$.

36. The flow cytometer of claim 35, wherein one or more detectors and the one or more further detectors are configured to collectively resolve both fluorescence and supracence simultaneously for each laser.

37. The flow cytometer of claim 34, wherein n is 1 to 12.

38. The flow cytometer of claim 37, wherein n is 4, 8, or 12, the imaging optics and one or more detectors or distinction regions thereof resolve four, eight, or twelve-color spectra with overlap of no more than 5%.

39. The flow cytometer of claim 37, wherein the eight-color spectra overlap is no more than 2%.

* * * * *